(12) United States Patent
Rosani et al.

(10) Patent No.: US 9,149,394 B2
(45) Date of Patent: Oct. 6, 2015

(54) MACHINE FOR MAKING ABSORBENT SANITARY ARTICLES, SUCH AS NAPPIES FOR BABIES OR INCONTINENCE PADS FOR ADULTS, SANITARY TOWELS OR THE LIKE

(75) Inventors: Marco Rosani, Vailate (IT); Davide Guarnieri, Milan (IT); Luca Bugini, Fara Gera D'Adda (IT); Davide Russo, Florence (IT); Matteo Piantoni, Albino (IT); Alberto Perego, Milan (IT)

(73) Assignee: GDM S.P.A. (IT)

( * ) Notice: Subject to any disclaimer, the term of this patent is extended or adjusted under 35 U.S.C. 154(b) by 114 days.

(21) Appl. No.: 13/981,131

(22) PCT Filed: Feb. 23, 2012

(86) PCT No.: PCT/IB2012/050825
§ 371 (c)(1),
(2), (4) Date: Jul. 23, 2013

(87) PCT Pub. No.: WO2012/114295
PCT Pub. Date: Aug. 30, 2012

(65) Prior Publication Data
US 2013/0299093 A1    Nov. 14, 2013

(30) Foreign Application Priority Data

Feb. 24, 2011    (IT) .............................. BO2011A0078

(51) Int. Cl.
*A61F 13/15*    (2006.01)
*B29C 65/16*    (2006.01)
(Continued)

(52) U.S. Cl.
CPC ..... *A61F 13/15699* (2013.01); *A61F 13/15723* (2013.01); *A61F 13/15739* (2013.01); *A61F 13/15756* (2013.01); *A61F 13/15804* (2013.01); *B23K 26/0063* (2013.01);
(Continued)

(58) Field of Classification Search
CPC .................... A61F 13/15739; A61F 13/15804; A61F 2013/15918; A61F 2013/15813; A61F 2013/15821; B29C 65/1619; B29C 65/002; B23K 26/206; B23K 26/0838; B23K 26/0063; B65H 35/04; Y10T 156/12; Y10T 156/1313; Y10T 156/1348
USPC ............. 219/121.63, 121.64, 121.73, 121.77, 219/121.85
See application file for complete search history.

(56) References Cited

U.S. PATENT DOCUMENTS 7,116,460 B2 * 10/2006 Griffin .......................... 359/245
2006/0283846 A1 * 12/2006 Lupinetti et al. ......... 219/121.73
(Continued)

FOREIGN PATENT DOCUMENTS

| EP | 1447068 | 8/2004 |
|---|---|---|
| EP | 1736272 | 12/2006 |

OTHER PUBLICATIONS

International Search Report and Written Opinion dated Jul. 2, 2012 from counterpart application.

*Primary Examiner* — Linda L Gray
(74) *Attorney, Agent, or Firm* — Timothy J. Klima; Shuttleworth & Ingersoll, PLC

(57) ABSTRACT

In a machine for making absorbent sanitary articles, such as nappies for babies or incontinence pads for adults, sanitary towels or the like, a plurality of operating stations are equipped with cutting and/or sealing devices for the materials of which the articles consist; all or some of the operating stations each being equipped with at least one laser unit for performing the cutting and/or sealing operation; the laser units all being connected to the same laser source.

12 Claims, 5 Drawing Sheets

(51) Int. Cl.
B23K 26/08 (2014.01)
B65H 35/04 (2006.01)
B29C 65/00 (2006.01)
B23K 26/20 (2014.01)
B23K 26/00 (2014.01)

(52) U.S. Cl.
CPC .......... *B23K 26/0838* (2013.01); *B23K 26/206* (2013.01); *B29C 65/002* (2013.01); *B29C 65/1619* (2013.01); *B65H 35/04* (2013.01); *Y10T 156/12* (2015.01); *Y10T 156/1313* (2015.01); *Y10T 156/1348* (2015.01)

(56) References Cited

U.S. PATENT DOCUMENTS

2007/0007353 A1* 1/2007 Danielson et al. ....... 235/462.46
2008/0305298 A1 12/2008 Lakshmi et al.

* cited by examiner

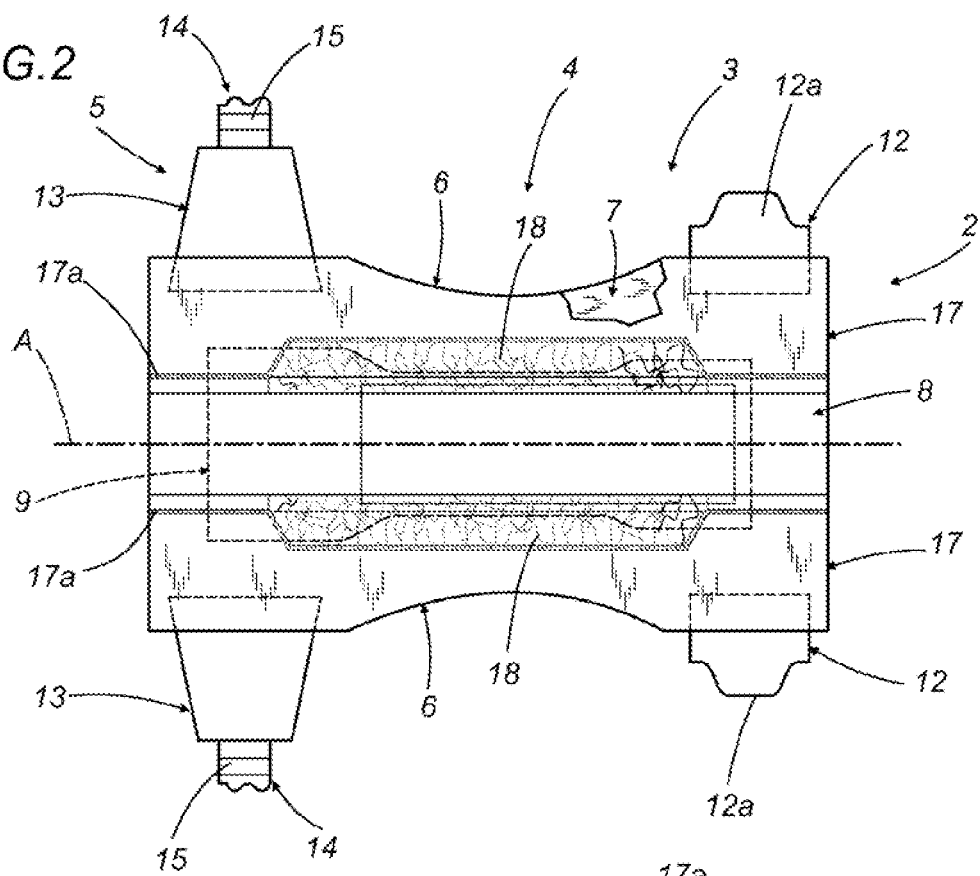
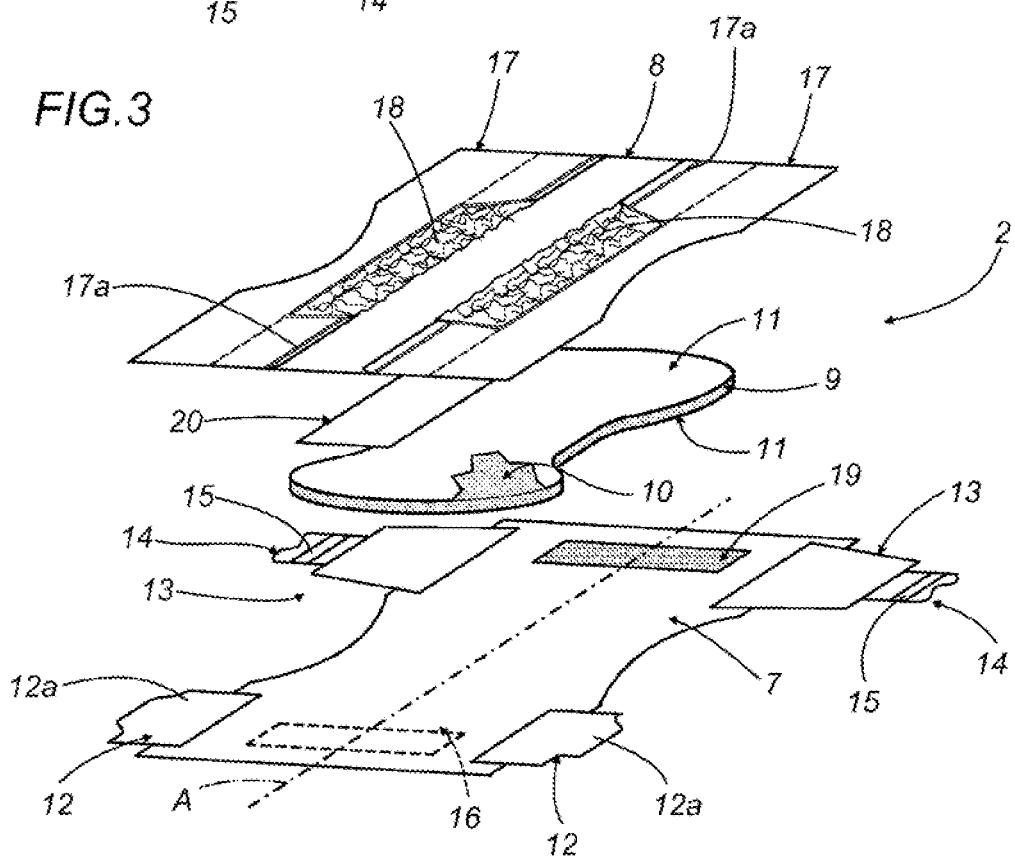

US 9,149,394 B2

MACHINE FOR MAKING ABSORBENT SANITARY ARTICLES, SUCH AS NAPPIES FOR BABIES OR INCONTINENCE PADS FOR ADULTS, SANITARY TOWELS OR THE LIKE

This application is the National Phase of International Application PCT/IB2011/050825 filed Feb. 23, 2012 which designated the U.S. and that International Application was published under PCT Article 21(2) in English.

This application claims priority to Italian Patent Application No. BO2011A000078 filed Feb. 24, 2011, which application is incorporated by reference herein.

TECHNICAL FIELD

This invention relates to a machine for making absorbent sanitary articles, such as nappies for babies or incontinence pads for adults, sanitary towels or the like

BACKGROUND ART

As is known, the above-mentioned articles are obtained by superposing a sheet of permeable material (non-woven fabric) on a sheet of impermeable material, and interposing an absorbent pad between them.

Generally, in addition to the above-mentioned basic components, the absorbent articles comprise various other components which make their structure, as well as their production, more or less complex. In particular, in the case of nappies for babies or incontinence pads for adults accessory components are normally used, for example, elastic bands, faecal barriers and lateral wings for fastening the nappies or incontinence pads around the waist of the users.

Prior art machines for making such products therefore comprise many feed means for the materials used to make the above-mentioned basic and accessory components.

More precisely, the sheets of impermeable and permeable materials and the various accessory components are made from continuous webs unwound from respective reels and separated into pieces, at operating stations or units, by suitable cutting devices. The various pieces are then joined to each other at stations in which gluing or sealing devices operate.

The devices for transversal cutting of the webs used in machines of the type considered comprise a blade able to move with a back-and-forth motion and an anvil, or a pair of rollers rotating in opposite directions, substantially at a tangent to each other and respectively equipped with a blade and a counter-blade.

In addition to the transversal cutting devices, there may be further cutting devices for shaping the articles to give them an anatomical shape. In particular, in the case of nappies for babies or incontinence pads for adults, they make two lateral leg openings at the central portion of the nappies for babies or incontinence pads for adults.

As is known, such cutting devices, all of the mechanical type, as well as having considerable dimensions, have the disadvantage of requiring frequent sharpening and regular substitution of the blades.

Moreover, due to the stresses which the reciprocal mechanical action of the blade and the counter-blade apply on the frame of the cutting device, the frame must be suitably sized. For that reasons, the frame is usually made of steel, with consequent negative repercussions in terms of weight, maneuverability during installation and transportation, and cost.

In addition to that, the large number of mechanical cutting units of the above-mentioned type significantly increases the noise emitted by the machine.

Similar considerations apply for the various sealing devices located along the production line. In fact, again, the presence of huge steel frames is a disadvantage in terms of dimensions, weight, maneuverability and cost.

DISCLOSURE OF THE INVENTION

The aim of this invention is to provide a machine for making absorbent sanitary articles, such as nappies for babies or incontinence pads for adults, sanitary towels or the like, which is economical to make, assemble and manage, and which at the same time has reduced overall dimensions and weight.

The above-mentioned aim is fulfilled with a machine for making absorbent sanitary articles, such as nappies for babies or incontinence pads for adults, sanitary towels or the like having the features described in one or more of the appended claims.

BRIEF DESCRIPTION OF THE DRAWINGS

This invention will now be described with reference to the accompanying drawings which show a non-limiting example embodiment, in which:

FIG. 2 is a plan view of an example of an absorbent sanitary article made by the machine of FIG. 1;

FIG. 3 is an exploded perspective view of the absorbent sanitary article of FIG. 2;

DETAILED DESCRIPTION OF THE PREFERRED EMBODIMENTS OF THE INVENTION

Figure 1:
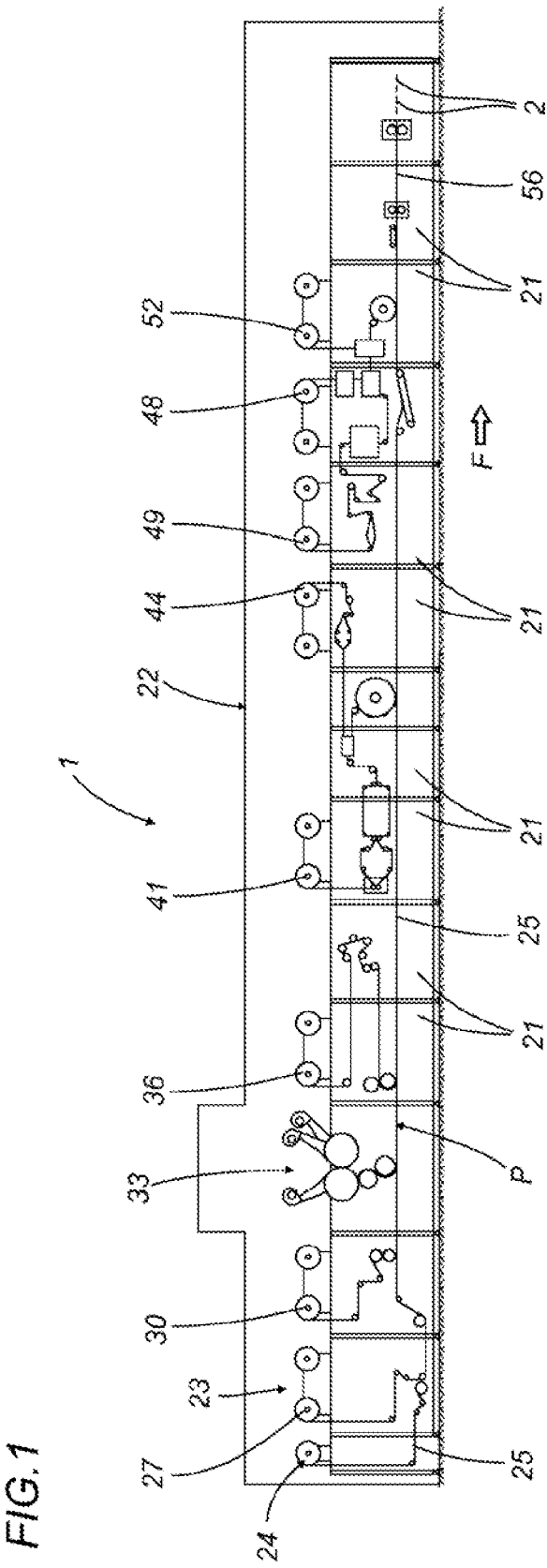
FIG. 1 is a schematic front view of a machine for making absorbent sanitary articles.

With reference to FIG. 1, the numeral 1 denotes in its entirety a machine for making absorbent sanitary articles 2, such as nappies for babies or incontinence pads for adults, illustrated in FIG. 2.

As shown in FIGS. 2 and 3, the articles 2 have a substantially rectangular shape.

The articles 2 comprise, aligned according to their longitudinal axis, labelled A, a front portion 3, a central portion 4 and a rear portion 5.

At the central portion 4 the articles 2 comprise a recess 6, or leg opening, formed by two arched stretches which are symmetrical relative to the axis A.

The articles 2 comprise a plurality of elements, which may be separated into main elements, or basic components, and accessory elements, or accessory components.

The main elements are a sheet 7 of impermeable material and a sheet 8 of permeable material (non-woven fabric), designed to respectively form the outer face and the inner face of the article 2.

The sheets 7 and 8 are superposed one on top of the other and interposed between them there is a third main element consisting of an absorbent pad 9, comprising a wad of cellulose fibre 10, enclosed between two sheets 11 of permeable material.

The accessory elements, which may vary in number and shape, are hereinafter described with reference to the sanitary article 2 illustrated in FIG. 3.

The numeral 12 denotes two shaped wings fixed to the inner face of the sheet 7, having a grip lobe 12a at the free end and projecting transversally to the axis A from the front portion 3.

The numeral 13 denotes two shaped wings, parallel with the wings 12, projecting from the rear portion 5.

Applied to each of the rear wings 13 there is a small wing 14 equipped with an adhesive strip 15, extending parallel with the axis A, designed to adhere, in use, to a corresponding front strip 16 applied to the front portion 3 of the outer face of the sheet 7. The wings 13 equipped with the small wings 14, together with the front strip 16, form means for fastening the article 2.

Sealed to the sides of the sheet 8 of permeable material there are two strips 17 of impermeable material for thickening and expanding its longitudinal edges, having an elasticated portion 18 at an intermediate stretch of them.

A further accessory element is an elastic band 19 applied, transversally to the axis A, to the inner face of the rear portion 5 of the sheet 7.

On the inner face of the sheet 8 of permeable material, in contact with the absorbent pad 9 and sealed along the border of the latter, there is a sheet of absorbent material 20, called the "acquisition layer", which is designed to render uniform the absorption by the surface of the pad 9.

Figure 4:
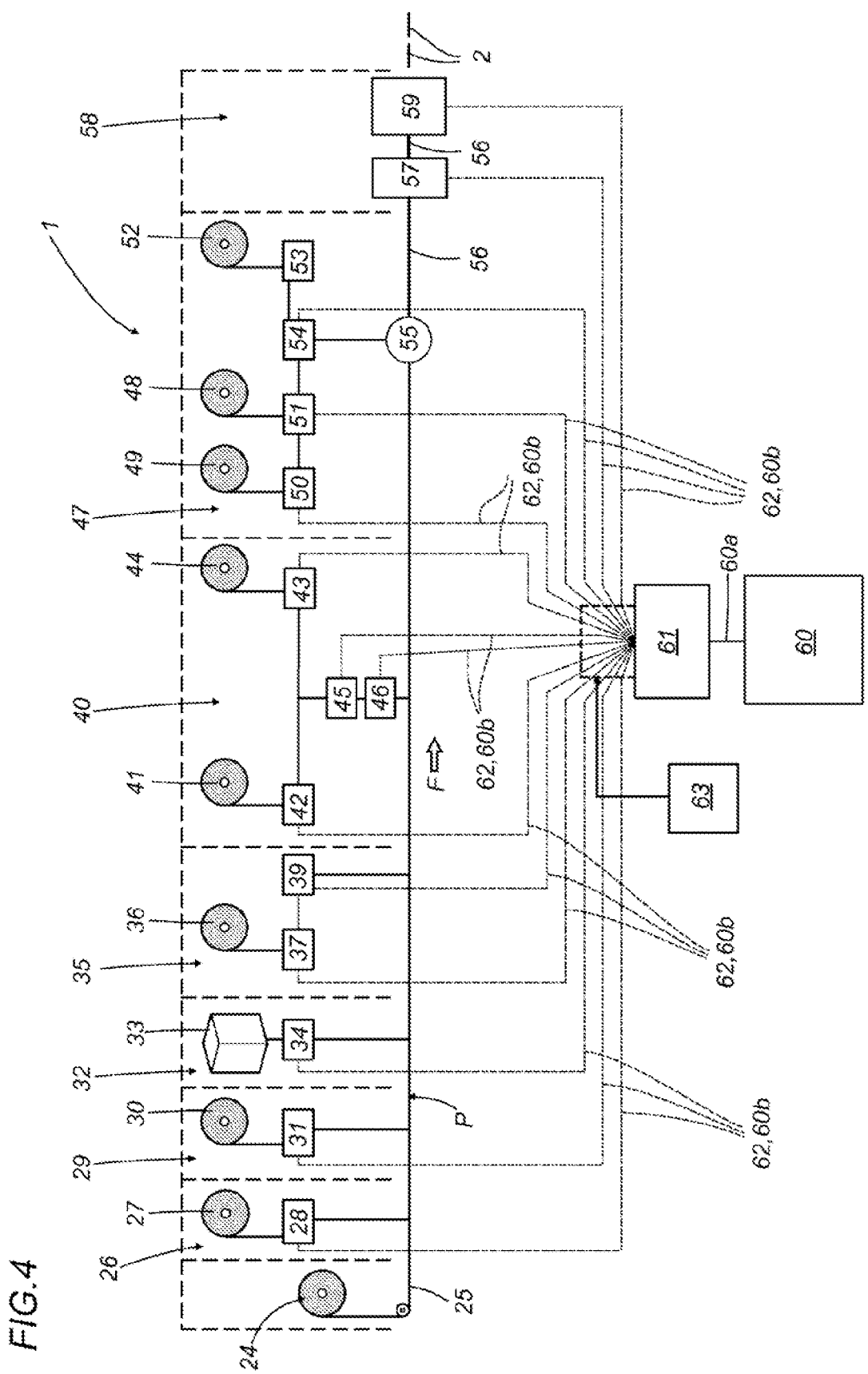
FIG. 4 is a block diagram relating to the machine of FIG. 1.

With reference to FIGS. 1 and 4, the machine 1 comprises a plurality of modules 21 which are drawn near each other, together forming a base 22 substantially having the shape of a parallelepiped delimited at the front by vertical wall 23.

The wall 23 constitutes the support for a plurality of operating units which are associated with each of the modules 21.

Said operating units comprise cutting and sealing devices, as well as units for unwinding reels of the various component materials of the articles 2, the reels being mounted shafts transversal to the wall 23.

Starting from the left end of FIG. 4, the machine 1 comprises at its infeed a unit for unwinding from a reel 24 a continuous web 25 of impermeable material which, once separated into pieces, will form the sheets 7.

Figure 5:
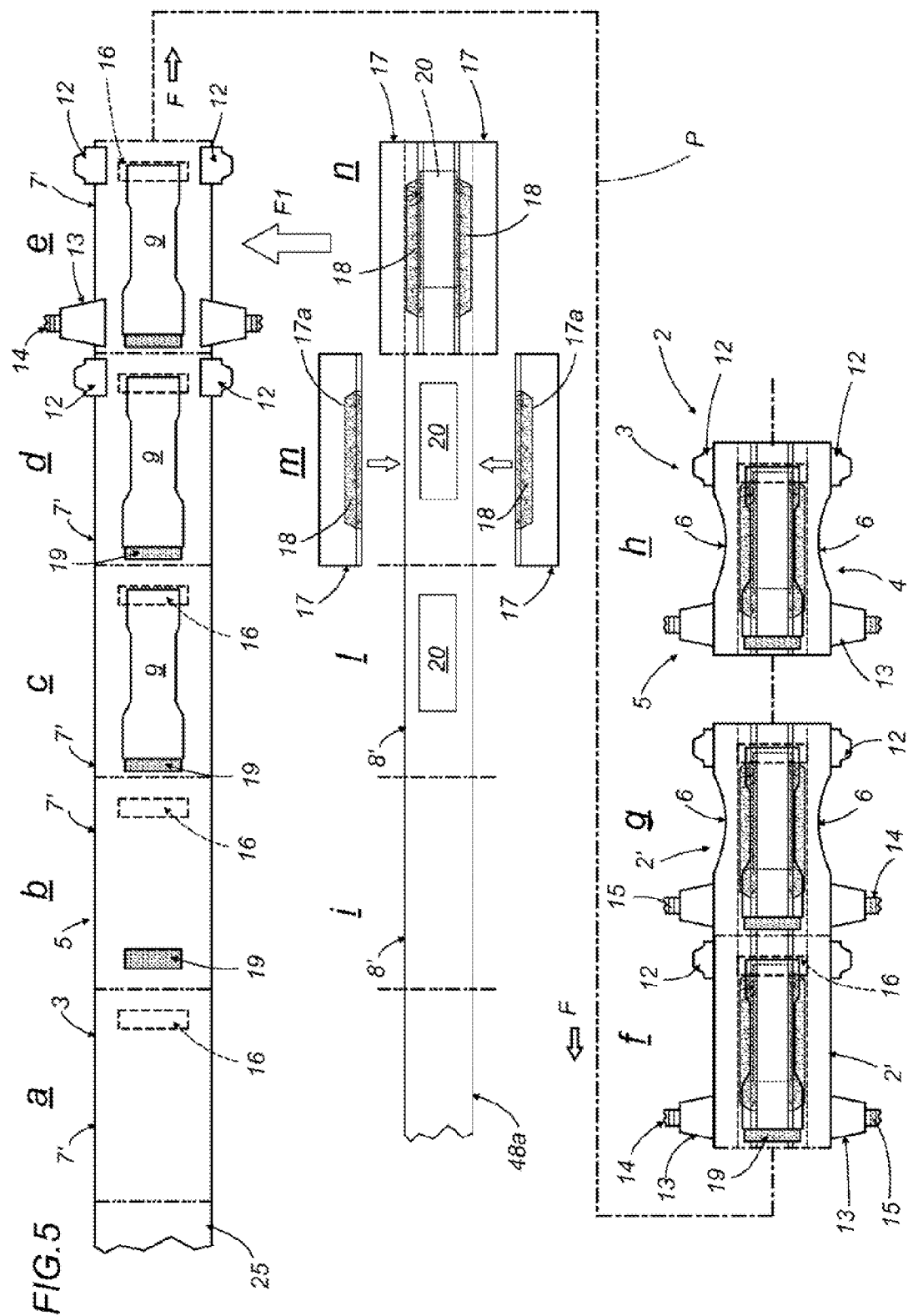
FIG. 5 is a plan view of the various steps for making the absorbent sanitary article of FIG. 3.

With reference also to FIG. 5, the continuous web 25 slides along a horizontal path P, in the direction indicated by the arrow F, through the operating units, which gradually make the article 2 by adding successive elements to each stretch, labelled 7', of web 25 corresponding to a sheet 7.

At a first operating unit 26 in the known way, using an adhesive substance, the front strip 16 transversal to the axis A is applied to the front portion 3 of the outer face of each stretch 7' of the web 25 (FIG. 5a).

The strips 16 are obtained by transversally cutting into pieces, with a cutting device which is a laser unit 28, a continuous web unwound from a reel 27.

At a second operating unit 29, using an adhesive substance, the strip 19 of elastic material is applied, transversally to the axis A, on the rear portion 5 of the inner face of each stretch T of the web 25 (FIG. 5b).

The strips 19 are obtained by transversally cutting into pieces, with a cutting device which is a laser unit 31, a continuous web unwound from a reel 30.

At a third operating unit 32, at the central zone of each stretch 7', an absorbent pad 9 is applied, comprising the wad 10 of cellulose fibre sandwiched between two pieces of 11 permeable material (FIG. 5c).

The pads 9 are made in a continuous succession by a unit, schematically illustrated with a block 33, according to a method described in patent IT2006BO00586, which is incorporated herein in its entirety for a complete description.

A cutting device comprising a laser cutting unit 34 separates the above-mentioned continuous succession into the individual pads 9.

Downstream of the operating unit 32 the web 25 passes through a fourth operating unit 35 for making the two front wings 12 and then application of said wings, with the grip lobe 12a outwards, on each stretch T of the web 25 (FIG. 5d).

Figure 6:
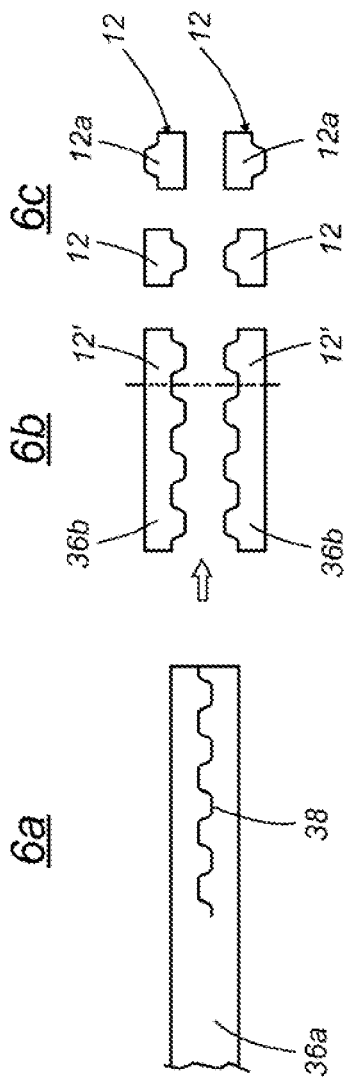
FIG. 6 is a schematic view of the various steps for making a first detail of FIG. 5.

With reference also to FIG. 6, the wings 12 are made from the same web 36a unwound from a reel 36.

A first cutting device which is a laser unit 37, able to move by oscillating transversally to the direction of feed of the web 36a, divides the web 36a longitudinally according to a line 38 which is substantially sinusoidal (FIG. 6a).

The two webs 36b generated by that cutting operation are divided into pieces 12' by respective cutting devices which are a laser unit 39 for making the individual wings 12 (FIGS. 6b, 6c).

The two front wings 12 are applied in the known way, with the lobes 12a outwards, on each stretch 7' of the web 25.

Downstream of the operating unit 35, along the path P, there is a fifth operating unit 40 for making the two rear wings 13, each provided with a respective small grip wing 14.

Figure 7:
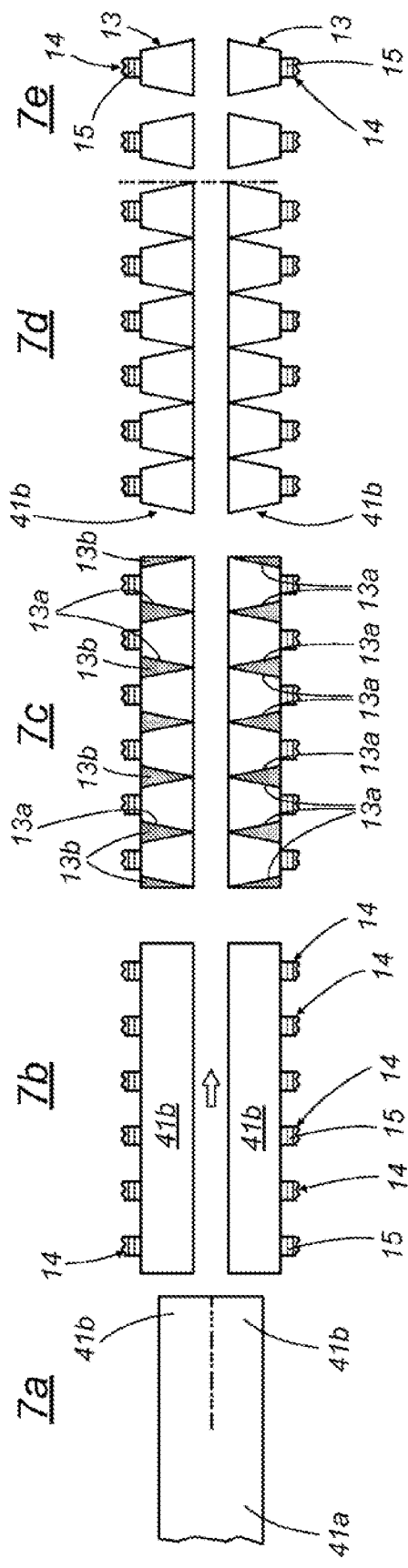
FIG. 7 is a schematic view of the various steps for making a second detail of FIG. 5.

With reference also to FIG. 7, the wings 13, which have a substantially trapezoidal shape, are made from the same web 41a unwound from a reel 41.

A first cutting device which is a fixed laser unit 42 divides the web 41a longitudinally into two identical webs 41b (FIG. 7a).

On each stretch 13', which will form an individual wing 13, on each of the webs 41b, an adhesive substance is used to apply a small wing 14 (FIG. 7b).

The small wings 14 are obtained by transversally cutting into pieces, with a cutting device which is a laser unit 43, a continuous web unwound from a reel 44, substantially according to the method already used to obtain the wings 12.

Two cutting devices comprising an oscillating laser unit, schematically illustrated with the block 45, make the oblique cutting lines 13a forming the triangular portions, labelled 13b, located between each pair of wings 13. Said portions 13b are eliminated using suction by a suction roller which is not illustrated.

A further cutting device which is a laser unit 46 completely separates the individual rear wings 13 from the respective continuous webs 41b.

Downstream of the unit 40 the wall 23 supports, close to its right-hand end, a sixth operating unit 47 comprising a unit for unwinding from a reel 48 a web 48a of permeable material (FIG. 5i).

A sheet 20 of absorbent material, constituting the "acquisition layer" is coupled to each stretch 8' which will form an inner sheet 8 of a sanitary article 2 (FIG. 5l).

The sheets 20 are obtained by dividing into pieces, with a cutting device which is a laser unit schematically illustrated with a block 50, a web unwound from a reel 49.

The sheets 20 are then applied to the web 48a by a sealing device which is a laser unit which is schematically illustrated with a block 51.

The lateral strips 17 of impermeable material are also applied to the stretches 8' of the absorbent web 48a (FIGS. 5m, 5n).

The strips 17 are obtained from a web unwound from a reel 52, through cutting operations carried out by a cutting device which is a laser unit 53.

A sealing device which is a laser unit 54 seals two strips 17, equipped with the above-mentioned elasticated portions 18, according to lines 17a close to the opposite longitudinal edges of each stretch 8'.

The web 48a equipped with the sheets 20 and the lateral strips 17 is guided (arrow F1) towards the path P and placed against the web 25 of impermeable material, in such a way that the stretches 8' are precisely superposed on the stretches 7'.

The block labelled 55 indicates a device for sealing the stretches 8' and 7' to each other along the respective borders for making a continuous web 56 comprising stretches 2' designed to form the articles 2 (station 5e).

The web 56 passes through a further operating unit 58, comprising a cutting device, consisting of a laser unit 57, able to move in such a way as to cut from each stretch 2' of web 56 two substantially semi-circular portions, thus giving said stretches 2' substantially the shape of an hourglass (FIG. 5g).

The operating unit 58 also comprises a cutting device which is a laser unit 59, which divides the web 56 into the individual finished articles 2.

With reference in particular to the diagram in FIG. 4, the block 60 indicate a diode-type laser source with predetermined power.

The laser source 60 is shared by all or some of the operating stations used for the cutting and/or sealing operations.

The laser source 60 emits a beam 60a, which is fed to the input of a splitter device of the known type, schematically illustrated with a block 61.

The splitter device 61 splits the beam 60a into a number of secondary beams 60b equal to the number of the above-mentioned laser units for cutting and/or sealing.

The means for conveying the secondary beams 60b to the respective laser units for cutting and/or sealing comprise fibre optic cables 62.

The use of optical fibres is particularly advantageous since the operating stations equipped with the respective laser units are usually remote from each other, that is to say, distributed along the articles production line in positions which are not adjacent.

According to an alternative embodiment, the diode-type laser source 60 is substituted with a QCL (quantum cascade laser) semiconductor-type laser source 60.

In this case, preferably, the laser source 60 emits at a frequency of between 2800 cm−1 and 3200 cm−1. In particular, preferably, the laser source 60 emits at a frequency of between 2900 cm−1 and 3100 cm−1. In that frequency range, the optimum frequency is substantially equal to 3000 cm−1. In fact, at that frequency, in temperature conditions equal to ambient temperature, experiments have shown that the various materials of which the absorbent articles are made demonstrate maximum energy absorption.

According to a further embodiment, the laser source 60 could be of the CO2 type. In that case, the means for conveying the secondary beams 60b to the respective laser units for cutting and/or sealing comprise tubular ducts (not illustrated).

The rated power of the source 60 may be substantially equal to the sum of the maximum powers necessary for each of the laser units connected to it.

If the various cutting and/or sealing operations are offset, in such a way that they do not all occur at the same time, the rated power of the laser source 60 may be suitably reduced. In this case, a central unit 63 is provided for selectively powering the individual laser units for cutting and/or sealing, the central unit being associated with the splitter device 61.

Preferably the laser source 60 is positioned remotely relative to the machine 1, since the secondary beams 60b are easily conveyed via the fibre optic cables 62.

Thanks to the use of the laser and the consequent substantial absence of mechanical stresses for the cutting and/or sealing operations, the individual operating stations can each be equipped with a frame made of plastic material. For example, each laser cutting device may comprise a respective frame made of plastic material. Similarly, each laser sealing device may comprise a respective frame made of plastic material.

It is apparent from the above description how this invention eliminates the various disadvantages of the prior art, caused by the use of mechanical cutting and sealing devices.

Full or partial substitution of the mechanical cutting and sealing devices with devices powered by a shared laser source 60, that is to say, a single laser source 60, allows considerable advantages over the conventional methods in terms of maintenance, noise, overall dimensions, overall weight, cost and maneuverability of the devices during installation and transportation.

The invention claimed is:

1. A machine for making absorbent sanitary articles, comprising:
 a plurality of operating stations equipped with devices for at least one chosen from cutting and sealing materials of the sanitary articles,
 a laser source;
 wherein at least two of the operating stations each comprise at least one laser unit for performing the at least one chosen from the cutting and sealing, the laser units being connected to a same single laser beam of the laser source;
 a splitter for splitting the same single laser beam emitted by the laser source into a plurality of secondary laser beams;
 conveying means for conveying one each of the secondary laser beams from the splitter to one each of the laser units for performing the at least one chosen from the cutting and sealing, wherein the conveying means comprise optical fibers.

2. The machine for making absorbent sanitary articles according to claim 1, wherein, the at least two of the operating stations are remote from each other.

3. The machine for making absorbent sanitary articles according to claim 1, wherein the same laser source is a diode laser source.

4. The machine for making absorbent sanitary articles according to claim 1, wherein the same laser source is a QCL (quantum cascade laser) semiconductor laser source.

5. The machine for making absorbent sanitary articles according to claim 4, wherein the same laser source emits at a frequency of between 2800 cm-1 and 3200 cm-1.

6. The machine for making absorbent sanitary articles according to claim 4, wherein the same laser source emits at a frequency of between 2900 cm-1 and 3100 cm-1.

7. The machine for making absorbent sanitary articles according to claim 4, wherein the same laser source emits at a frequency substantially equal to 3000 cm-1.

8. The machine for making absorbent sanitary articles according to claim 1, wherein the same laser source is of a CO2 laser source.

9. The machine for making absorbent sanitary articles according to claim 1, wherein a rated power of the same laser source is equal to a sum of maximum powers absorbed by the laser units.

10. The machine for making absorbent sanitary articles according to claim 1, wherein a rated power of the same laser source is less than a sum of the powers absorbed by the laser units of the devices for the at least one chosen from cutting and sealing, there being a central unit for selectively powering the laser units.

11. The machine for making absorbent sanitary articles according to claim 1, wherein the same laser source is located in a remote position relative to the machine.

12. The machine for making absorbent sanitary articles according to claim 1, wherein the operating stations each comprise a respective frame made of plastic material.

\* \* \* \* \*